United States Patent [19]

Schickle

[11] Patent Number: 5,407,546

[45] Date of Patent: Apr. 18, 1995

[54] METHOD FOR HIGH-RESOLUTION TWO-DIMENSIONAL ELECTROPHORESIS AND DEVICE FOR CARRYING OUT THE SAME

[75] Inventor: Hanspeter Schickle, Tübingen, Germany

[73] Assignee: ETC Elektrophorese-Tecknik Westermeier & Schickle GmbH, Leonberg, Germany

[21] Appl. No.: 170,528

[22] Filed: Dec. 20, 1993

[30] Foreign Application Priority Data

Dec. 24, 1992 [DE] Germany .................. 42 44 082.3

[51] Int. Cl.⁶ ............................................. C07K 3/28
[52] U.S. Cl. ........................ 204/182.1; 204/182.8; 204/182.9; 204/299 R
[58] Field of Search ............... 204/182.1, 182.8, 182.9, 204/299 R

*Primary Examiner*—John Niebling
*Assistant Examiner*—Edna Wong
*Attorney, Agent, or Firm*—Darby & Darby

[57] ABSTRACT

For high-resolution two-dimensional electrophoresis comprising the steps of carrying out, on a gel base, at first a first separation process in a first direction and then a second separation process in a direction vertical to the first direction by a technique different from that of the first separation, for example by molecular screening, it is proposed to use as a basis a dry gel consisting of a single piece and extending in the two dimensions and to hydrate the dry gel selectively in a strip-like area for carrying out the isoelectric separation in the first dimension, while the remaining gel area retains its dry gel configuration, to then perform the separation in the first dimension in the selectively hydrated area, and to hydrate thereafter the remaining electrophoresis area of the gel for carrying out the second separation process.

10 Claims, 4 Drawing Sheets

1 DIMENSION: IEF

2 DIMENSION: SDS-PAGE

1. DIMENSION: IEF

2. DIMENSION: IMMUNO-ELECTROPHORESIS

ELECTROPHORETIC MIGRATION INTO A GEL CONTAINING ANTI-BODIES

SELECTIVE RE-HYDRATION WITH ANTIBODIES reproducible re-equilibration in the SDS buffer, reproducible transfer and good contact between the first and the second dimension, and of course the need to check if all proteins have effectively migrated out from the first dimension.

METHOD FOR HIGH-RESOLUTION TWO-DIMENSIONAL ELECTROPHORESIS AND DEVICE FOR CARRYING OUT THE SAME

FIELD OF THE INVENTION

The invention relates to a method high-resolution, two-dimensional electrophoresis, and a device for carrying out this method.

BACKGROUND OF THE INVENTION

The combination of two different electrophoresis methods has been known in many different forms and has been employed, for example, for separating part of the fractions from complex protein mixtures by means of a first electrophoresis step, and then to proceed with the separation by a second method, based on different parameters, in order to ensure that, for example, proteins that are irrelevant for the given problem will not influence the separation to be actually achieved, or in order to ensure in the case of complex protein mixtures that these are fractionated into all their different proteins, if possible, so as to obtain an overall map of the protein composition and to enable individual proteins to be detected.

A general summary of high-resolution 2D electrophoresis methods based on a polyacrylamide gel is provided by the paper by Michael J. Dunn and Arthur H. Burghes entitled "Review", published in the magazine "Electrophoresis 1983", 4, 97–116, so that there is no need to give a detailed description of these methods at this point; reference is made insofar to the before-mentioned publication and also to some additional publications corresponding to DE-OS 2,107,092; DE-OS 2,013,840; DE-PS 32,32,685 and/or the summary contained on page 31 of the book "Elektrohporese-Praktikum" by Dr. Rainer Westermeier, VCH Verlangsgesellschaft mbH, 6940 Weinheim. Reference is made to this book also with respect to the general understanding of electrophoretic separation processes, and the instruments, chemical substances and gels required for them.

In summary, in can be noted that for carrying out two-dimensional electrophoresis the methods most commonly employed to this day consist in using, for isoelectric focussing (separation after charging) in the first dimension, a gel having the largest possible pores and being different from the gel used for the second dimension, so that screening effects are avoided from the very beginning. In order to achieve the desired high reproducibility of the measured values, it is desirable that variations occurring when pouring the gel be possibly avoided so that it is preferred to make use of ready-to-use gels. This gives rise, however, to another problem because it is necessary in this case to introduce into the gel matrix what is known as chaotropic agents (urea) in order to avoid aggregates between proteins and complex formation, and because dissolved urea is chemically instable when such ready-to-use gels are to be stored.

It has also been known in this connection to use cylindrical gels, slab gels, round gels with nylon thread (millipore) or film-supported strips for separation in the first dimension.

Thereafter, the transfer from the first to the second dimension must be effected, for which purpose IEF spaghettis or IEF strips on carrier film, placed on vertical or horizontal SDS gels, are suited best among all options available, with the resulting necessity to achieve reproducible re-equilibration in the SDS buffer, reproducible transfer and good contact between the first and the second dimension, and of course the need to check if all proteins have effectively migrated out from the first dimension.

For the second dimension, i.e. the separation by molecular weight (SDS electrophoresis) one normally uses a fine-pore gel having a high screening effect and a high pH value; but the high pH value gives ready-to-use gels a limited shelf life. If in this connection a discontinuous buffer system were used in order to achieve efficient separation, then—as is generally known—the buffers of ready-to-use gels would diffuse into each other during storage.

In connection with the problems arising with two-dimensional electrophoresis, reference is made finally to two recent publications, namely U.S. Pat. No. 4,874,490 (Hochstrasser) and the Japanese Patent No. JP 58105053 A2 (Hitachi).

The Hochstrasser patent uses two different gels for two-dimensional electrophoresis on a common carrier, for example a glass plate, namely a strip gel for the first dimenion and further a slab gel, the two gels being separated by an isolating area. The two gels are prepared ready for use, which means that they are wet gels, the strip gel containing in any case chaotropic agents and the slab gel being suited for carrying out SDS electrophoresis (SDS=sodium dodecyl sulfate).

For separation in the second dimension, the isolating area is removed in order to establish the necessary electric contact between the two gels. Consequently, there may arise in this case just the same problems as described before, namely instability of the ready-to-use gel containing the chaotropic agent, and in particular the necessity for the proteins to migrate into the slab gel via the previously isolating area. The Hochstrasser patent differs insofar only very little from the previously known, physically separate ready-to-use gels for two-dimensional electrophoresis, with the only difference that the first dimension is realized in geometric proximity to the second dimension.

In contrast to the above, the before-mentioned Japanese Patent JP 58105053 A2 proposes a rather complex and time-consuming method of carrying out two-dimensional separation, making use of a pore-gradient gel and doing without the usual SDS separation in the second dimension.

Consequently, the polyacrylamide matrix defined by its monomer concentration varies in concentration from, for example, between 4% and 20 or 25%, the lowest concentration that can be regarded as having particularly large pores being used for carrying out the separation in the first dimension in the usual way, by isoelectric focussing, while thereafter, as a result of the pore gradient variation, separation is effected by molecular size rather than by molecular weight. Another difficulty may present itself in connection with this two-dimensional separation method insofar as carrier ampholytes, i.e. so-called amphoteric buffer substances, each having different isoelectric points, must have been introduced into the entire gel for creating the necessary pH gradient.

Now, it is the object of the present invention to provide a high-resolution two-dimensional electrophoresis method which is carried out in a single gel and which can be realized with particular ease and at particularly low cost.

ADVANTAGES OF THE INVENTION

The invention achieves this object by means of the features specified in claim 1 and/or in sub-claim 8 and provides the advantage over the known methods that both isoelectric focussing in the first dimension and SDS separation by molecular weight is carried out based on a genuinely uniform, common gel (single-gel 2D electrophoresis) using a dry gel which as such eliminates all problems connected with the usual wet ready-to-use gels, such as reduced shelf life, chemical instability, mechanical instability of the matrix, and which also avoids other variations that may occur during gel pouring, i.e. during polymerization at the site, with a view to achieving a sufficiently high degree of reproducibility.

Still, the invention succeeds in carrying out the separation in the two dimensions according to absolutely mutually independent parameters.

In fact, the present invention succeeds in realizing a long-cherished dream that could not be realized heretofore, namely to have the possibility to apply the sample on a single gel, to let the first separation take place, to then re-buffer the system in a simple way, and to finally carry out the separation in the second dimension.

Specifically, the present invention also provides that the separation in the first dimension is effected by isoelectric focussing, and in the second dimension by SDS screening by molecular weight.

Another advantage of the invention lies in the fact that it is not necessary to transport any gel strips or gel spaghettis during transition from the first to the second dimension and that no physical change of the gel matrix used is required.

Hence, it is possible even in cases where only simple equipment is available, i.e. for example in developing countries or under less sophisticated laboratory conditions, to carry out perfect, highly reproducible and highly precise two-dimensional electrophoretic separation processes, it being possible, due to the invention, to eliminate a number of manipulations that would otherwise be necessary for two-dimensional separation, and also to avoid other faults and possible variations.

Due to the fact that the invention provides a single gel, which being a dry gel is hydrated and wetted or impregnated with the corresponding chemicals only at the very moment of use, both dimensions, i.e. the isoelectric focussing step and the subsequent SDS electrophoresis step, can be carried out on the same gel so that there is no need for any gel manipulations or transfer from one gel to the next, with all the sources for faults and confusion connected with such steps. Likewise, there is no need for pouring gels or for mixing buffer solutions. The gels being washed before the drying process, the dry gels do no longer contain any poisenous substances. The fact that no gel transfer has to be effected between the first and the second dimensions results in easy handling;

high reproducibility;

the possibility to separate large protein quantities with high resolution; and the possibility to perform this work in a "casual" way, as it is now drastically simplified.

As for purposes of evaluation of the results, the first dimension is always dyed, it is always possible to check the transition from the first to the second dimension.

Finally, it is now possible, due to the improved equilibration rendered possible by the invention, to convert even critical proteins into SDS miscellae, and also to run the first dimension as a native process.

The measures specified in the sub-claims permit advantageous further developments and improvements of the invention. In this connection, it is regarded as a particular advantage that it is now possible to carry out simultaneously two 2D separation processes per gel, with both samples being processed under identical conditions.

Finally, another embodiment of the invention consists in that during the original preparation of the gel in the factory a large-pore gel matrix is provided in the strip area of the first dimension, while the remaining gel area, which follows the matrix without any transition, takes the form of a fine-pore polyacrylamide gel acting as a molecular screen for effecting the separation in the second dimension, by molecular weight.

Another, particularly advantageous embodiment and application of the two-dimensional electrophoresis method provides for zone-electrophoretic separation or isoelectric focussing in the first dimension and for immuno- or affinity-electrophoretic separation in the second dimension. In carrying out this method, the fractionated proteins are caused to migrate electrophoretically from the gel of the first dimension into a gel layer containing, for example, monovalent or polyvalent antibodies (mostly immunoglobulins) or for example lectines (these react high specifically to certain sugar residues in glycoproteins). These reactive additives bind specific proteins spefificically and quantitatively and form with them giant molecules that do not migrate any further in the gel and which then can be detected in a simple way. This method is widely used, above all in clinical routine, being highly specific and quantifiable.

BRIEF DESCRIPTION OF THE DRAWING

Certain embodiments of the invention will now be described in greater detail by reference to the drawing in which:

FIG. 4 shows the preparations and the starting position of the common gel for carrying the SDS electrophoresis on the focussed proteins, while

FIG. 6 finally shows the common 2D gel with two 2D electrophoresis processes being carried out simultaneously and, below the same, a perspective view of the equilibrating chamber in which the 2D gel is soaked and re-equilibrated in preparation of the second separation process; while

DETAILED DESCRIPTION OF THE EMBODIMENTS OF THE INVENTION

The basic idea underlying the present invention consists in that, starting out from a uniform dry specimen gel, which insofar represents a single molecule, the gel is first selectively hydrated in strip form, i.e. localized in the first dimension, the necessary IEF mixture being preferably applied simultaneously during this step, then carrying out the separation in the first dimension and soaking thereafter the 2D gel, whose separating gel area is still dry and has not been affected in any way by the selective hydration of the strip area of the first dimension, then re-equilibrating the IEF and carrying out thereafter the SDS electrophoresis process.

The process starts out from a thin or ultra-thin gel matrix in a horizontal two-dimensional electrophoretic separation system; the gel matrix is arranged on a thin carrier film and may, according to a first embodiment, have a uniform polymerisation structure and consist, for example, of polyacrylamide or agarose, as usual.

The invention is based on the realization that the hydration of only a partial area of the dry gel that forms the starting basis remains absolutely confined to the area that has come into contact with the hydrating liquid and/or IEF mixture; this makes itself felt by the fact that after completion of the selective hydration step a clear plateau forms in the strip area of the first dimension, which means that all of the liquid mixture applied has been completely absorbed, and is also locally retained, by the strip-like gel area of the dry gel, and that no part of the mixture is transferred to neighboring areas, at least not within the periods of time relevant in the present context, i.e. for example within 4 to 5 hours.

Figure 1:
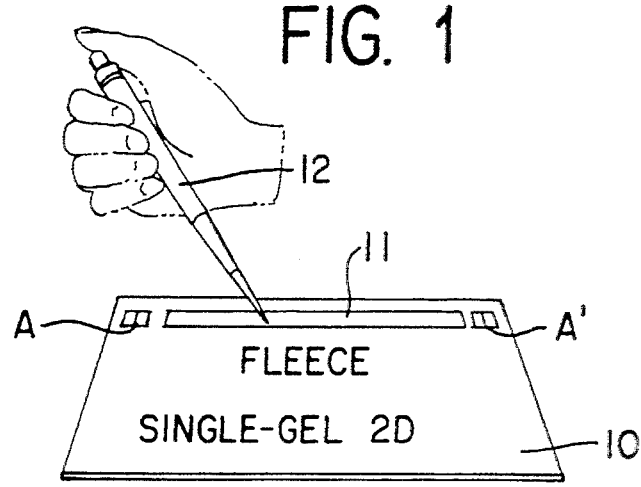
FIG. 1 shows a perspective diagram illustrating the formation of an IEF plateau in the common basic initial dry gel, by application of the IEF mixture by means of a pipette.

Thus, for producing such an IEF plateau, one places a strip-like fleece 11, or a strip of any other easily wettable material, on the marginal area of the dry gel layer 10, as shown in FIG. 1.

Generally, this can be effected in such a way that the dry gel layer, selectively covered by a fleece, is inserted bubble-free (with the carrier film of a suited material facing the bottom) into a trough that contains a small quantity of water in order to get a firm hold for the subsequent manipulations and to avoid drying-out during the soaking time. Thereafter, a predetermined quantitity (for example 2 ml) of an IEF mixture is dispensed upon the fleece using a pipette 12 and is, to the extent possible, distributed uniformly over the fleece 11.

Figure 2:
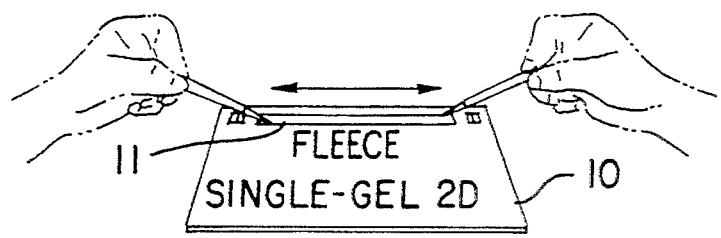
FIG. 2 illustrates the step of stretching a strip-like fleece, which serves as a carrier for the IEF mixture, to both sides.

After some time, the fleece 11 will extend in length, so that it will then be useful to grip the two ends of the fleece between tweezers and to stretch it slightly—as illustrated in FIG. 2—in order to remove any folds.

One then permits the dry gel, after it has been locally hydrated in this way, to rest in covered condition for a predetermined period of time, for example for 40 min. in the case of the native IEF mixture and 60 min. in the case of a urea mix of 8 mol/liter.

At the end of the predetermined period of time, the fleece is pulled off using a pair of tweezers, whereupon it can be seen that the IEF plateau formed in this way, which had been covered by the fleece, has fully expanded.

Figure 3:
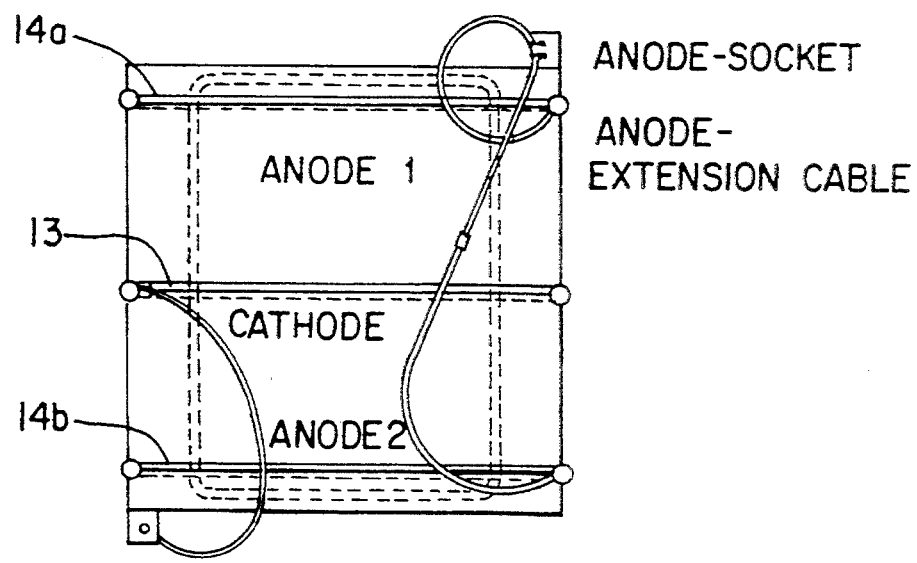
FIG. 3 shows the arrangement of the electrodes for the isoelectric focussing step (first dimension), where two 2D electrophoresis processes can be carried out simultaneously.

The further process is then as illustrated in FIG. 3; since two 2D electrophoresis processes are carried out simultaneously, there is provided a common central cathode 13, while two anodes 14a, 14b are provided in the two end portions and are electrically connected with corresponding electrode holders. This need not be explained here in more detail, except for the fact that before the 2D gel is placed on a cooling plate, any water is removed from the bottom surface of the film by pulling the latter across a filter paper.

Thereafter, the separation process of the first dimension is run, the different phases (introduction of the sample, main focussing 1 and main focussing 2) being carried out with different electric data and for different durations.

After completion of the IEF separation process, the specimen gel (2D gel) is soaked and re-equilibrated. In detail, this is effected by filling a predetermined quantity of gel buffer into a suitable dish, placing the 2D gel bubble-free on the grate of the dish, with the coating in downward direction, and stirring the cold gel buffer for a predetermined period of time, for example for 10 min. in the case of a native IEF mixture of the first dimension, or 13 min. in the case of a 8 mol/liter urea mix.

Figure 6:
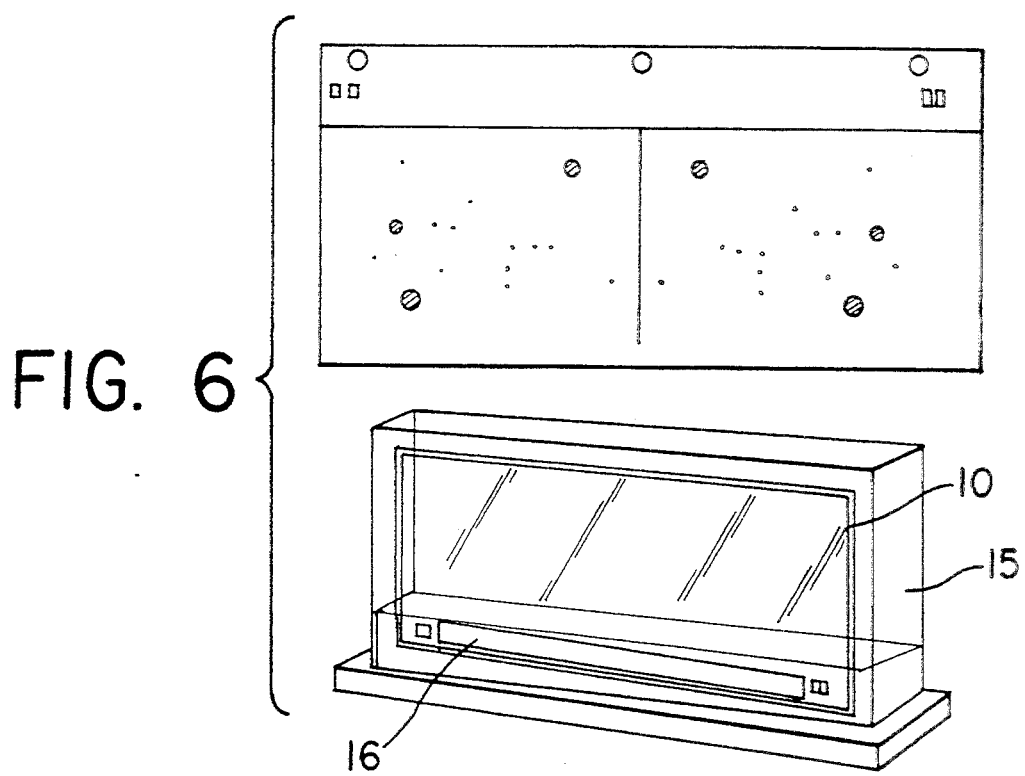

Thereafter, the 2D gel is removed from the dish and placed vertically into an equilibrating chamber for selective equilibration in a hot specimen gel equilibrator, as indicated at 15 in FIG. 6 where a so-called Verteq equilibration chamber is shown. The selective equilibration serves for preparing the focussed proteins, and at the same time the 2D gel 10 with the IEF plateau 16 gets into the hot Verteq bath.

The process just described can be followed once more by a certain dwelling time of the 2D gel in the cold stirred gel buffer.

The steps of soaking and re-equilibrating the 2D gel are followed by the SDS electrophoresis process of the second dimension; the gel is removed from the stirrer or the Verteq bath, the electrodes are mounted, and SDS electrophoresis is run.

In detail, one proceeds in such a way that after the 2D gel has been withdrawn, it is placed on a filter paper, with its film side in downward direction, and the film side is freed from the SDS buffer by pulling the gel across the paper.

Figure 4:
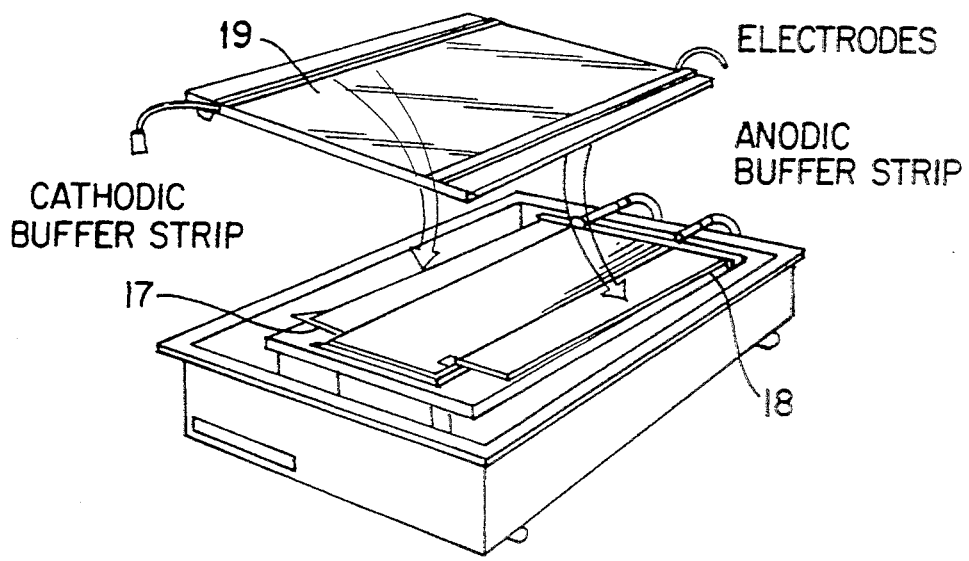
Figure 5:
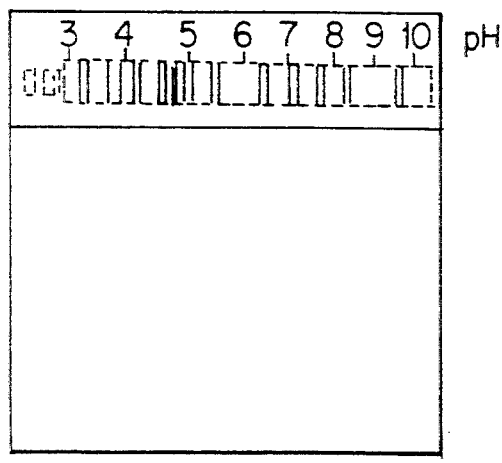
FIG. 5 illustrates—for improved understanding—on the one hand the separation in the first dimension and, laterally beside the same, the separation in the second dimension, where the focussed proteins migrate over the specimen gel surface in crosswise direction relative to the first separation direction.
Figure 5:
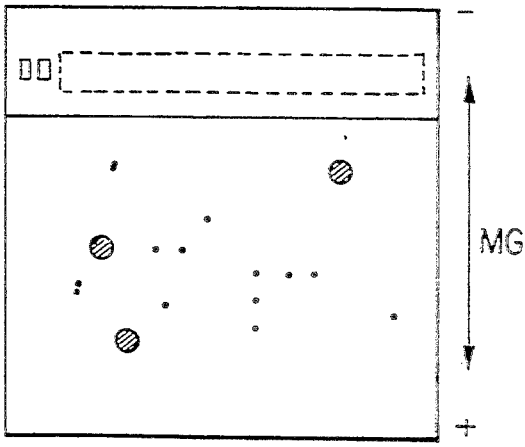

Thereafter, the gel surface may also be dried by means of an electrophoresis paper, whereupon the 2D gel is placed on a cooling plate, with the film in downward direction, as illustrated in detail in FIG. 4.

Electrode cartons in the form of cathodic and anodic buffer strips 17 and 18, respectively, are placed on both sides of the gel surface in the marginal area thereof; the electrodes, which are part of a covering glass plate 19, are connected to the cathodic and anodic buffer strips, and the corresponding values are set on the respective current supply means in order to cause the SDS electrophoresis to proceed.

Given the fact that the two separation processes proceed preferably according to the basic principle of isoelectric focussing (first separation) and SDS electrophoresis (second separation) and that these two separation methods of the first and the second dimensions are known as such to the man of the art, it is not necessary at this point to further discuss additional details and/or the necessary ingredients and chemicals; however, an advantageous embodiment may consist in basing the process on a discontinuous polyacrylamide gel, i.e. one having larger pores in the strip area for the separation of the first dimension than in the electrophoresis surface—an arrangement that can easily be accommodated during production of the gel. After drying, one then obtains the stable initial dry gel of the present invention which has unlimited shelf life. In use, one then re-hydrates selectively a partial area, initially for the isoelectric focussing process, while the remainder of the dry gel is re-hydrated with the SDS buffer only later, during subsequent SDS equilibration of the focussed proteins.

Figure 7:
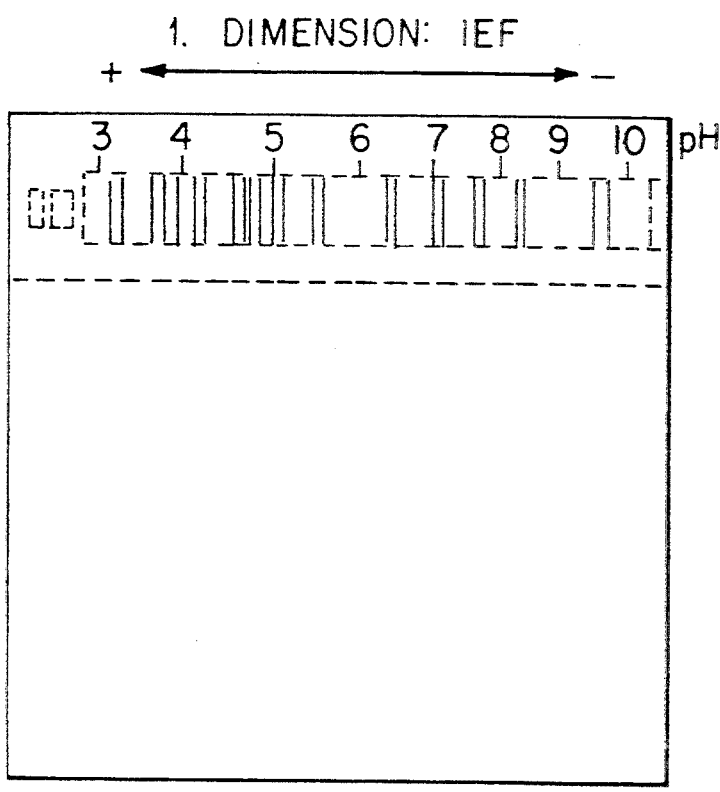
FIGS. 7, 8 and 9 show, as an additional example, the application of the 2D electrophoresis process according to the invention for carrying out an immuno- or affinity-electrophoretic separation process.
Figure 8:
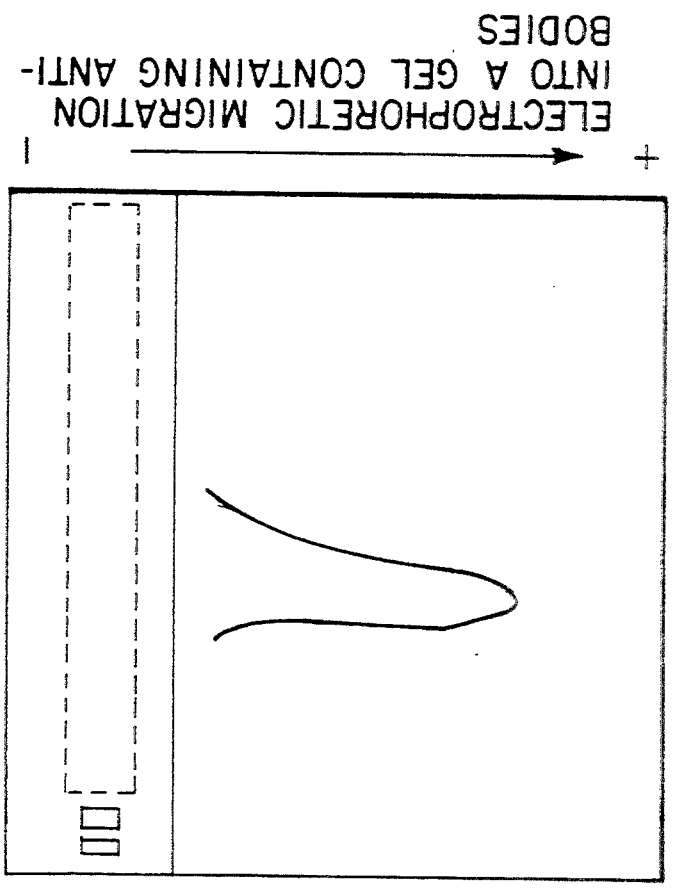
Figure 9:
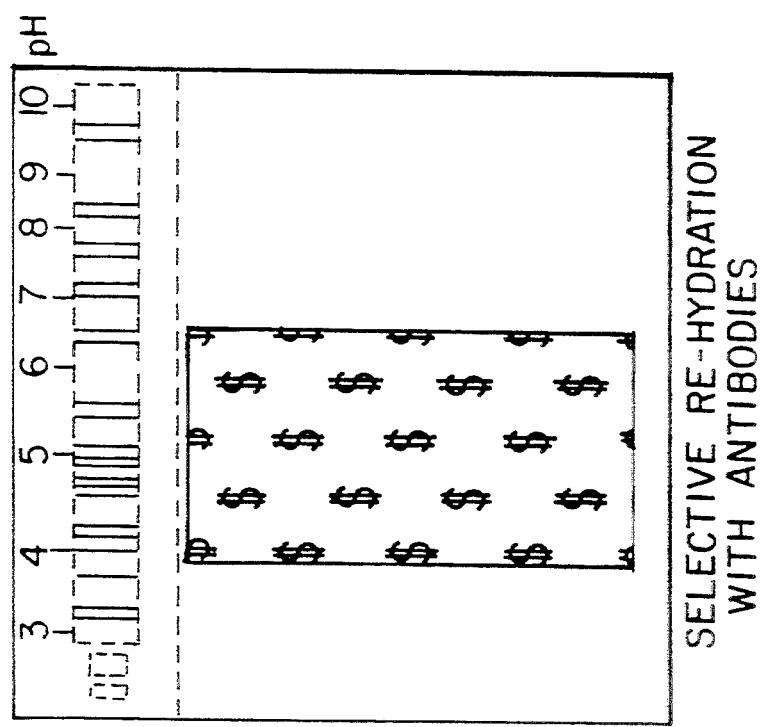

The two-dimensional electrophoresis process further permits zone-electrophoretic separation or isoelectric focussing in the first dimension and immuno- or affinity-electrophoretic separation in the second dimension. For this purpose, one causes the fractionated proteins to migrate electrophoretically from the gel of the first dimension into a gel layer containing, for example, monovalent or polyvalent antibodies (mostly immunoglobulins) or for example lectines (these react highly specifically to certain sugar residues in glycoproteins) (see FIGS. 7 to 9). These reactive additives bind specific proteins spefificically and quantitatively and form with them giant molecules that do not migrate any further in the gel and which then can be detected in a simple way. This method is widely used, above all in clinical routine, being highly specific and quantifiable.

Specifically, one further re-hydrates for the second dimension a selective part of the surface of the second dimension with a solution of, for example, antibodies or, for example, lectines, using another fleece 11' of suitable size. Given the fact that in many cases the position of the proteins to be located is known already in the first dimension, only a relatively small surface must be soaked with the expensive additives, whereby a considerable amount of costs can be saved (antibodies and lectines are very expensive). Thereafter, the entire gel is re-hydrated with the corresponding buffer, and in doing so the proteins are simultaneously re-buffered. Then, the electrophoresis process in the second dimension is run.

The advantages achieved by this modification are the same as those described before, except that a further selective re-hydration is added.

Lastly, it should be mentioned that the claims, and especially the main claim, are attempts at putting the invention into words without a comprehensive knowledge of the prior art and therefore without limiting prejudice. The right to regard all features presented in the description, the claims, and the drawings, both individually and in any combination, as essential to the invention, and to record them in the claims, is therefore reserved, as is the right to reduce the features contained in the main claim.

I claim:

1. A method for high-resolution two-dimensional electrophoresis comprising the steps of carrying out at first, on a gel base, a first separation process in a first direction by isoelectric focussing or any other electrophoretic separation technique, and performing thereafter a second separation process in a direction vertical to the first direction by a technique different from that of the first separation,
    wherein said gel base comprises a dry gel made of a single piece and extending in two dimensions, selectively hydrating the dry gel in a strip-like area for carrying out the first separation in the first dimension, while the remaining gel area retains its dry gel configuration, performing thereafter the separation in the first dimension in the selectively hydrated area, and hydrating the remaining electrophoresis area of the gel for carrying out the second separation process.

2. A method according to claim 1, wherein the dry gel is mounted on a carrier film and is free from any chaotropic substances and sodium dodecyl sulfate buffers and any additives, and is later re-hydrated for use.

3. A method according to claim 1, wherein a selective hydration for the isoelectric focussing separation or any other electrophoretic separation in the first dimension is performed by applying on a marginal area of the dry gel a fleece strip, which is made of an easily wettable material, and dispensing upon the fleece strip by means of a pipette, the isoelectric focusing mixture or another electrophoresis buffer.

4. A Method according to claim 3, wherein after the isoelectric focussing mixture or the other electrophoresis buffer has been effective there on the fleece strip for a predetermined period of time, a local plateau is formed on the dry gel in the isoelectric focussing area by expansion of the gel, whereupon the isoelectric focussing process, or the other electrophoretic separation process of the first dimension, is carried out by suitable connection to the corresponding electrodes.

5. A method according to claim 4, wherein, based on the isoelectric focussing or electrophoresis plateau formed by the selective hydration process, two 2-dimensional electrophoresis processes are carried out simultaneously by applying protein samples, which are to be examined, on both sides of the plateau.

6. A method to claim 5, wherein upon completion of the isoelectric focussing process, or any other electrophoresis process differing from that of the first dimension, the remaining dry gel area is likewise rehydrated by an sodium dodecyl sulfate buffer, whereafter the proteins that have been separated in the first dimension are selectively subjected to an sodium dodecyl sulfate equilibration or any other re-buffering process.

7. A method according to claim 6, wherein the sodium dodecyl sulfate equilibration or the other re-buffering processes, as well as re-hydration of the remaining dry gel area, are performed simultaneously using an sodium dodecyl sulfate buffer or any other buffer.

8. A method according to claim 3, wherein a selective part or selective parts of the area of the second dimension are rehydrated by one or more solutions of antibodies ore lectines, by means of another fleece, or other fleece pieces, for the second dimension.

9. A device for high-resolution two-dimensional electrophoresis where, using a gel base, at first a first separation process is carried out in a first direction by isoelectric focussing and then, using the gel base, the second separation is performed in a direction vertical to the first direction, wherein a single dry gel is provided as a basis and means are provided for selectively hydrating at first the dry gel in a partial area for carrying out the first separation so that a strip-like area of the dry gel is soaked and expanded uniformly with the mixtures to be used for carrying out the first separation process.

10. A device according to claim 9, wherein the single dry gel is mounted on a supporting film, said single dry gel has a large-pore structure in the area to be selectively hydrated.

* * * * *